United States Patent [19]

Seiler et al.

[11] Patent Number: 5,547,852
[45] Date of Patent: Aug. 20, 1996

[54] COMPOSITION CONTAINING THE P40 SUBUNIT OF INTERLEUKIN-12

[75] Inventors: Friedrich-Robert Seiler, Marburg; Roland Kurrle, Niederweimar; Klaus-Dieter Langner, Marbug, all of Germany

[73] Assignee: Behringwerke Aktiengesellschaft, Marburg, Germany

[21] Appl. No.: 235,321

[22] Filed: Apr. 29, 1994

[30] Foreign Application Priority Data

May 7, 1993 [DE] Germany .................. 43 15 127.2
Apr. 12, 1994 [EP] European Pat. Off. .......... 94105595

[51] Int. Cl.⁶ .................. C12Q 1/02; G01N 33/567; A61K 45/05
[52] U.S. Cl. .................. 435/29; 435/7.21; 435/4; 530/351; 424/85.2
[58] Field of Search .................. 435/29, 7.21, 4; 530/351; 424/85.2

[56] References Cited

U.S. PATENT DOCUMENTS

5,296,353  3/1994  Ochoa et al. .................. 435/7.23

FOREIGN PATENT DOCUMENTS

9005147  5/1990  WIPO .

OTHER PUBLICATIONS

Ling et al. "Demonstration of The Roles of IL-12 Subunits In Receptor Binding & Signal Transduction" J Immunol. 150(8 Pt 2) 207A. Abstract 1182 1993.
Mattner et al. "The Interleukin-12 subunit P40 Specifically Inhibits Effects of The Interleukin-12 Heterodimer" Eur J. Immunol. 23 2202-2208 1993.
Gubler et al. "Studies On The Expression of Interleukin-12 Subunit mRNAs In Mice" J Cell. Biochem. Supplement 17B 112 Abstract E510 1993.
Kobayashi et al., "Identification And Purification Of Natural Killer Cell Stimulatory Factor (NKSF), A Cytokine With Multiple Biologic Effects On Human Lymphocytes", *J. Exp. Med.*, vol. 170:827–845, (1989).
Schoenhaut et al., "Cloning And Expression Of Murine IL-12", *The Journal of Immunology*, vol. 148:3433–3440, (1992).
Germann et al., "Components Of An Antigen-/T Cell Receptor-Independent Pathway Of Lymphokine Production", *Eur. J. Immunol.*, vol. 21:1857–1861, (1991).
Wolf et al., "Cloning of cDNA For Natural Killer Cell Stimulatory Factor, A Heterodimeric Cytokine With Multiple Biologic Effects On T And Natural Killer Cells", *The Journal of Immunology*, vol. 146:3074–3081, (1991).
Podlaski et al., "Molecular Characterization Of Interleukin 12", *Archives Of Biochemistry And Biophysics*, vol. 294:230–237, (1992).
Zettlmeissl et al., "Efficient Expression System For Human Antithrombin III In Baby Hamster Kidney Cells", *Behring Inst. Mitt.*, vol. 82:26–34, (1998).
Koehler et al., "Continuous Cultures Of Fused Cells Secreting Antibody Of Predefined Specificity", *Nature*, vol. 256:495–497, (1975).
Mengel et al., "An Activated Murine B Cell Lymphoma Line (A-20) Prodices A Factor-like Activity Which Is Functionally Related To Human Natural Killer Cell Stimulatory Factor", *Eur. J. Immunol.*, vol. 22:3173–3178, (1992).
Dunn et al., "An Alternative Pathway Of Induction Of Lymphokine Production By T Lymphocyte Clones", *The Journal Of Immunology*, vol. 142:3847–3856, (1989).

*Primary Examiner*—Mindy Fleisher
*Assistant Examiner*—Nancy J. Degen
*Attorney, Agent, or Firm*—Foley & Lardner

[57] ABSTRACT

The present invention relates to a composition containing the p40 subunit of interleukin-12, hereinafter referred to as p40/IL-12 and to methods of diagnosis and treatment of disorders associated with disregulation of the immune system.

12 Claims, 1 Drawing Sheet

Stimulation of the production of gamma-interferon by mIL-12

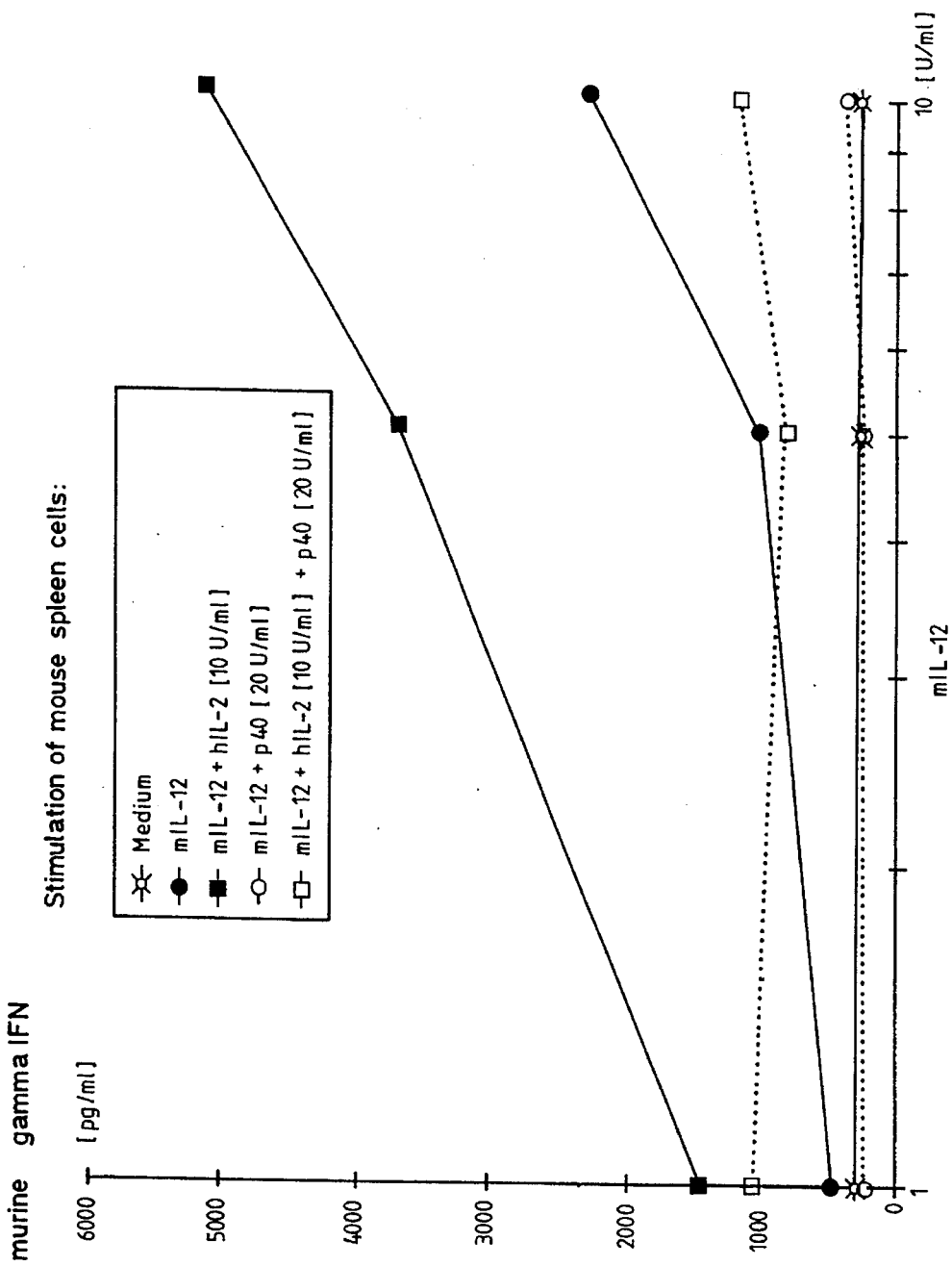

COMPOSITION CONTAINING THE P40 SUBUNIT OF INTERLEUKIN-12

BACKGROUND OF THE INVENTION

The present invention relates to a pharmaceutical composition containing the p40 subunit of the cytokine interleukin-12 ("IL-12"). This composition is particularly suitable for use in the treatment of disorders which are associated with disregulation of the immune system.

Immune reactions are supported by different T-cell populations. Depending on the type of the immune reaction, T-cell help is provided either by Type 1 T-helper Cells (TH1) or by Type 2 T-helper cells (TH2). As far as is known to date, TH1 cells differ from TH2 cells, in particular, by producing cytokines.

Dunn et al., *J. Immunol.* 142:3847 (1989), demonstrated that TH1 clones produce gamma interferon (gamma-IFN), provided they are cultivated in the presence of accessory cells and IL-2. In addition, Germann et al., *Eur. J. Immunol.* 8:1857–1862 (1991), demonstrated that a soluble mediator is required for the synthesis of gamma-IFN by TH1 cells. It emerged from comparative investigations that the mediator designated TSF is identical to murine IL-12. Recently, Mengel et al., *Eur. J. Immunol.* 22:3173–3178 (1992), likewise described, in the supernatant of the activated murine B cell lymphoma line A-20, a soluble factor which stimulates gamma-IFN production in T-cells. The soluble factor described by Mengel et al. in the A-20 supernatant was compared functionally by Wolf et al., *J. Immunol.* 156:3074 (1991), with a so-called "human natural killer cell stimulatory factor" (NKSF) and was postulated to be the murine analog of human IL-12. It is known that IL-12 and NKSF, which may be identical, both stimulate gamma-IFN synthesis. The function of IL-12 or NKSF is not naturally limited to the stimulation of gamma-IFN production. Inter alia, IL-12 or NKSF also affects the function of (i) natural killer cells, so-called NK or LGL cells, (ii) IgE production and (iii) increases IL-12-induced proliferation of resting peripheral mononuclear cells.

It has been shown that IL-12 is composed of two subunits which are designated p35 and p40. Podlaski et al., *Arch. Biochem. Biophys.* 294:230–237 (1991). Murine IL-12 was found to have an almost identical structure. Schoenhaut et al., *J. Immunol.* 148:3433–3440 (1992). While the p40 subunit of IL-12 apparently does not possess any IL-12-specific bioactivity on its own, the p40 subunit is of considerable importance for the bioactivity of the complete IL-12 molecule. It has been speculated that p40 interacts directly with the cellular IL-12 receptor. There remains no evidence, however, of the particular role played by p40 in the immune function of IL-12.

It is well established in the literature that disregulation of cytokine production and cytokine effects may cause acute and chronic disorders of the immune system and their associated sequelae. In addition, influencing cytokine-mediated activities represents a potential therapeutic approach for many different cytokine-related disorders. Therefore, there is considerable interest in evaluating and affecting the function of IL-12 in mammalian subjects.

SUMMARY OF THE INVENTION

Therefore, an objective of the present invention is the generation of a composition which can be used to diagnose and treat pathological conditions which are associated with disregulation of IL-12-mediated activities.

Surprisingly, it has been discovered that the p40 subunit of IL-12 ("p40/IL-12") can be used to inhibit IL-12-mediated activities. Therefore, it now is possible to achieve the aforementioned diagnostic and therapeutic goals by using p40/IL-12 to interfere with these activities.

In satisfying the foregoing objective, there is provided a composition comprising natural or recombinant p40/ILH-12 of mammalian origin. The p40/IL-12 may be modified, for example, it may comprise only an active fragment, or a homolog or addition, deletion or substitution variant of p40/IL-12. The p40/IL-12 may be derived from any mammal but the preferred embodiment of the invention relates to p40/IL-12 having the human amino acid sequence.

In another embodiment, the present invention relates to the use of p40/IL-12 in the detection and treatment of pathological conditions which are associated with disregulation of IL-12-mediated activities. Similarly, the use of IL-12 to detect and treat the abnormal expression of p40/IL-12 also is contemplated. Examples of such abnormal or pathological conditions are autoimmune diseases such as systemic lupus erythematosus, Wegener's syndrome or rheumatic arthritis, bacterial or viral infections and certain solid tumors or leukemias.

BRIEF DESCRIPTION OF THE DRAWINGS

FIG. 1. This graph shows the IL-12 dose dependent stimulation of gamma-IFN production from mouse spleens, in the absence and presence of the p40/IL-12 subunit.

DETAILED DESCRIPTION OF THE INVENTION

The invention relates to a diagnostic or pharmaceutical composition comprising p40/IL-12 and its use in the detection or treatment of disorders involving altered levels of IL-12. In addition, the present invention also involves the use of IL-12 to detect the presence of p40/IL-12 in biological samples and to treat diseases relating to the abnormal expression of p40/IL-12 in vivo.

IL-12 and the p40/IL-12 subunit thereof may be obtained by different technologies, for example, by genetic engineering, biochemical isolation and purification from IL-12 from natural sources or from hybridoma cells which secrete IL-12 or p40/IL-12. The following different methods of obtaining IL-12 and p40/IL-12 are described. As other methods exist, the invention should not be construed as limited to the methods described below.

For the isolation of recombinant murine IL-12 and the p40 subunit of mIL-12, mRNA was isolated using standard techniques from murine spleen cells and then converted into double-stranded cDNA. Sambrook et al., *MOLECULAR CLONING: A Laboratory Manual*, Cold Spring Harbor Laboratory Press, Cold Spring Harbor, N.Y. (1989). Using the primers and conditions described in Schoenhaut et al., *J. Immunol.* 148:3433 (1992), polymerase chain reaction ("PCR") was carried out which resulted in the generation of an approximately 800 base-pair fragment.

The PCR fragment was sequenced by standard techniques. Sambrook et al. (1989). The experimentally determined cDNA sequence was found to be identical to the published sequence for the murine p40 subunit. The PCR fragment for the p35 subunit was isolated and sequenced in an analogous manner.

In order to confirm that the biological activities described below do indeed result from IL-12 and/or the p40 subunit, the PCR fragments were cloned, individually or in combination, into the vector pABstop and stably expressed in BHK-21 cells using a standard process. Zettlmeiβl, *Behring Inst. Mitteilungen* (*Communications*) 82,26 (1988). It was possible to isolate both biologically active mIL-12 and a biologically active p40 subunit of mIL-12 from culture supernatants of transfected BHK-21 cells.

The supernatant of the murine B-cell lymphoma line A-20 (American Type Culture Collection, ATCC TIB208), which was activated in accordance with Mengel et al. (1992), served as the source of natural IL-12. The soluble mediator described by Mengel in the A-20 supernatant is compared functionally with NKSF and is regarded as the murine analog of human IL-12. Spleen cell preparations, which were prepared and activated in accordance with the method described by Germann et al. (1991), represented a further source of natural IL-12. Comparative investigations demonstrated that the TSF described by Germann et al. (1991) is identical to mIL- 12.

A hybridoma cell which secreted murine p40/IL-12 was isolated and used as the natural source of the subunit. To prepare this hybridoma cell, $1-10 \times 10^6$ murine T-cells, cultivated in the presence of syngeneic monocytes ($1 \times 10^5$/ml) and recombinant murine GM-CSF (50 ng/ml), were injected subcutaneously together with complete Freund's adjuvant ("CFA") into female rats (Lewis strain, Zentralinstitut für Versuchstiekunde, Hannover). Two further immunizations took place at intervals of 2 weeks, when the same cell quantities were injected intraperitoneally. The animals were sacrificed 3 days after the last injection and the spleen cells were fused with the cells of the murine myeloma cell line SP2/FO in accordance with the well known standard procedure of Köhler and Milstein, *Nature* 256:495 (1975). The growing hybridoma cell was selected in accordance with standard procedures. Investigations which were carried out as described in Example 1 demonstrated that supernatants of one of the isolated hybridoma inhibited gamma-IFN release. Following the published process of Kobayashi et al., *J. Exp. Med.* 170:827 (1989), a secreted protein was purified from the culture supernatant of this hybridoma cell. After purification by reverse-phase HPLC, the isolated protein fraction was separated by SDS-PAGE, a dominant protein band being found in the region of about 40–45 kD. Sequence comparisons confirmed that this isolated protein was identical to murine p40/IL-12.

For pharmaceutical application, effective quantities of the compounds of the invention may be administered to a patient or an animal by any of the various methods, for example, orally as in capsules or tablets or parenterally, for example, intravenously, intramuscularly, intracutaneously or subcutaneously in the form of sterile solutions or suspensions. The free products, while effective themselves, may be formulated and administered in the form of their pharmaceutically acceptable derivatives in order to increase stability, for convenience of crystallization, increased solubility and the like. Salts are the most common form of derivative.

Because p40/IL-12 has the capacity to interfere with IL-12 induction of target cells, it is possible to measure the amount of IL-12 or p40/IL-12 in a biological sample by examining IL-12 induction. For example, a biological sample can be used to stimulate target cells that are susceptible to IL-12 induction. The addition of p40/IL-12 to the target cells, prior to or simultaneously with the addition of the sample, will result in blocking of IL-12 induction if IL-12 is present in the sample. By comparing IL-12 induction by the biological sample in the absence and presence of p40/IL-12, it is possible to determine whether IL-12 is present in the sample. Similarly, when a biological sample is suspected of containing p40/IL-12, the ability of the sample to inhibit IL-12 induction of susceptible cells is measured.

The principle of action is the same for in vivo therapy as it is for the diagnostic context. For certain disorders, it may prove beneficial to decrease IL-12 induction of target cells. Because of the ability of p40/IL-12 to inhibit IL-12 induction of target cells, the administration of effective amounts of a pharmaceutical composition containing p40/IL-12 would be expected to interfere with IL-12 activity and, hence, the induction of target cells. In an analogous manner, the pathologic production of p40/IL-12 may result in an abnormally low degree of IL-12 stimulation in vivo. Therefore, administration of exogenous IL-12 would be expected to minimize or reverse the effects of p40/IL-12 inhibition.

The pharmaceutical compositions of the present invention may be orally administered, for example, with an inert diluent such as water or a physiologically acceptable buffer. Likewise the active compounds may be admixed with an edible carrier, enclosed in gelatine capsules or compressed into tablets.

For oral therapeutic administration, the active compounds may be incorporated with excipients such as starch or lactose and used in the form of tablets, troches, capsules, elixirs, suspensions, syrups, wafers, chewing gum and the like. The amount of active compound in such compositions is such that an effective dosage will be obtained. The tablets, pills, capsules, troches and the like may also contain, for example, the following ingredients: a binder such as microcrystalline cellulose, gum tragacanth or gelatin, a disintegrating agent such as alginic acid, Primogel, cornstarch and the like; a lubricant such as magnesium stearate or Stenotex; a glidant such as collodial silicon dioxide; and a sweetening agent such as sucrose or saccharin or a flavoring agent such as peppermint and methyl salicylate or fruit flavoring. When the dosage unit form is a capsule, in addition to the materials of the above type, a liquid carrier such as a fatty oil is included. Other dosage unit forms may contain various materials which modify the physical form of the dosage unit, for example, as coatings. Thus, tablets or pills may be coated with sugar, shellac, or other enteric coating agents. A syrup may comprise sucrose as a sweetening agent and certain preservatives, dyes, colorings and flavors. Materials used in preparing these various compositions should be pharmaceutically pure and non-toxic in the amounts used.

For parenteral therapeutic administration, the amount of active compound in solutions or suspensions used is such that an effective dosage is obtained. The solutions or suspensions also may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment tonicity such as sodium chloride or dextrose.

The pharmaceutical is finally prepared by a process which is known per se to the person skilled in the art. p40/IL-12, i.e., the active compound, is employed in an effective concentration either as such or in combination with suitable pharmaceutical additives or auxiliary substances as well as physiologically acceptable solvents.

As stated above, the p40/IL-12 may be modified, for example, it may comprise only the active fragment of p40/IL-12 responsible for inhibit IL-12 mediated activities.

Such a fragment can be determined by routine methods, for example, by systematic testing of p40/IL-12 fragments in assays as described herein to determine which fragments inhibit IL-12 mediated activities. Alternatively, a homolog or addition, deletion or substitution variant of p40/IL-12 may be used, again provided that the homolog or variant possesses the ability of p40/IL-12 to inhibit IL-12 mediated activities. Conservative substitutions, therefore, are expressly contemplated.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Example 1

Inhibition by p40/IL-12 of the IL-12-induced release of gamma-IFN

In order to induce the release of gamma-IFN, $5 \times 10^6$ spleen cells from BALB/c mice were cultivated for 48 h in the presence or absence of recombinant or natural mIL-12 and IL-2 in concentrations given. After 48 h of culture, the supernatant was harvested from the spleen cells and centrifuged until cell-free. The content of gamma-IFN in the supernatant is determined in commercially available ELISA systems, e.g., Intertest TM-gamma, Mouse IFN-gamma ELISA kit, Genzyme. The gamma-IFN from the culture supernatant of activated spleen cells was quantified by comparison with recombinant murine gamma-IFN (Genzyme). A typical experiment is presented in FIG. 1. As the data demonstrate, cultivation of murine spleen cells with IL-12 led, in a dose-dependent manner, to the release of >5 ng/ml of gamma-interferon. If spleen cells were preincubated at the beginning of the culture with recombinant murine p40/IL-12 or with hybridoma supernatant which contained the natural p40 subunit of mIL-12, however, stimulation with mIL-12 resulted in at least a 50% inhibition of the IL-12-dependent synthesis of gamma-IFN. This example demonstrates that both recombinant p40/IL-12 and hybridoma supernatant containing the natural p40/IL-12 are able to inhibit the IL-12-induced synthesis of gamma-IFN.

Example 2

Inhibition by p40/IL-12 of the IL-12-induced activity of NK cells

Spleen cells from C57BL/6 mice were cultivated in serum-free Iscove's medium at a cell density of $5-10 \times 10^6$ cells/ml in 24-well Costar plates at 37° C. for 18 h. The spleen cells were cultivated in different concentrations of recombinant or natural murine IL-12. After 18 h, the cells were harvested, the number of living cells determined by Trypan Blue staining and the cytolytic activity determined in a 5-hour $^{51}$Cr release test. YAC-1 cells (ATCC TIB160) were used as target cells. $^{51}$Cr-labeling of target cells, and the $^{51}$Cr-release assay were carried out according to standard methods. Schoenhaut et al., *J. Immunol.* 148:3433–3440 (1992). The ratios of effector cells to target cells were typically 100:1, 50:1, 25:1 and 12.5:1. The percent specific cytolysis was calculated as:

$$\frac{\% \text{ lysis of the experimental group} - \% \text{ spontaneous lysis}}{\% \text{ maximum lysis} - \% \text{ spontaneous lysis}) \times 100}$$

By preincubating C57BL/6 spleen cells with IL-12, it was possible to increase specific cytolysis by at least 5-fold, as compared with the starting control (ratio 50:1). If spleen cells were additionally preincubated with recombinant or natural murine p40/IL-12 under the same culture conditions, however, IL-12-dependent cytolysis was inhibited by at least 50%.

It will be apparent to those skilled in the art that various modifications and variations can be made to the compositions and processes of this invention. Thus, it is intended that the present invention cover such modifications and variations, provided they come within the scope of the appended claims and their equivalents.

What is claimed is:

1. A method of detecting IL-12 in a biological sample, comprising the steps of:
    (a) providing a system comprising cells that produce a detectable biological response to IL-12;
    (b) adding to said system a defined amount of p40/IL-12 effective to inhibit a biological response by said cells to IL-12, and a defined amount of a biological sample; and
    (c) detecting said biological response.

2. The method according to claim 1, wherein p40/IL-12 has an amino acid sequence which is human.

3. The method according to claim 1, further comprising step (d) comparing said response to the response generated by said system in the absence of said p40/IL-12.

4. The method according to claim 1, wherein said step (b) comprises adding said defined amount of p40/IL-12 simultaneously with or subsequent to adding said defined amount of biological sample.

5. A method of detecting p40/IL-12 in a biological sample, comprising the steps of:
    (a) providing a system comprising cells that produce a detectable biological response to IL-12;
    (b) adding to said system a defined amount of IL-12 effective to elicit a biological response by said cells, and a defined amount of a biological sample; and,
    (c) detecting said biological response.

6. The method according to claim 5, wherein p40/IL-12 has an amino acid sequence which is human.

7. The method according to claim 5, further comprising step (d) comparing said biological response to the biological response generated by said system in the absence of said defined amount of said biological sample.

8. The method according to claim 5, wherein said step (b) comprises adding said defined amount of IL-12 simultaneously with or subsequent to adding said defined amount of biological sample.

9. A method for inhibiting biological activities mediated by IL-12 in a subject, comprising the step of administering to said subject a pharmaceutical composition comprising a biologically inhibitorily effective amount of a natural or recombinant p40/IL-12 or a biologically inhibitorily fragment, derivative, homolog, or an addition, deletion or substitution variant thereof.

10. A method according to claim 9, wherein said p40/IL-12 comprises the amino acid sequence of human p40/IL-12.

11. A method for the detection of pathological conditions associated with the disregulation or abnormal expression of IL-12-mediated biological activities in a subject, comprising the steps of administering to said subject a biologically inhibitorily effective amount of natural or recombinant p40/IL-12 or a biologically inhibitorally fragment, derivative, homolog, or addition, deletion or substitution variant thereof, and testing said subject for said IL-12 biological activity.

12. A method of claim 11, wherein said p40/IL-12 comprises the amino acid sequence of human p40/IL-12.

* * * * *